United States Patent [19]  [11] 4,070,395
Fujise et al.  [45] Jan. 24, 1978

[54] PROCESS FOR THE PREPARATION OF 4,4'-DIAMINOSTILBENE-2,2'-DISULFONIC ACID OR ITS SALTS

[75] Inventors: Masatomo Fujise, Wako; Koji Isobe, Yono, both of Japan

[73] Assignee: Nippon Kayaku Kabushiki Kaisha, Tokyo, Japan

[21] Appl. No.: 717,272

[22] Filed: Aug. 24, 1976

Related U.S. Application Data

[63] Continuation of Ser. No. 711,725, Aug. 11, 1976, abandoned.

[30] Foreign Application Priority Data

Aug. 13, 1975 Japan .................................. 50-97520

[51] Int. Cl.$^2$ ............................................ C07C 143/62
[52] U.S. Cl. .................................................... 260/510
[58] Field of Search ........................................ 260/510

[56] References Cited

U.S. PATENT DOCUMENTS

| | | | |
|---|---|---|---|
| 2,455,807 | 12/1948 | Redmon et al. | 260/510 |
| 3,936,497 | 2/1976 | Hirata et al. | 260/510 |
| 3,989,743 | 11/1976 | Braden et al. | 260/510 |

*Primary Examiner*—Nicky Chan
*Attorney, Agent, or Firm*—Russell & Nields

[57] ABSTRACT

4,4'-diaminostilbene-2,2'-disulfonic acid (hereinafter abbreviated as DAS) or its alkali salt (abbreviated as DAS-salt) are prepared by catalytic hydrogenation of 4,4'-dinitrostilbene-2,2'-disulfonic acid (hereinafter abbreviated as DNS) or its alkali salt (abbreviated as DNS-salt). The catalytic hydrogenation is carried out using Raney nickel catalyst in the presence of dicyandiamide in water at a temperature in the range of 50°–120° C under an elevated hydrogen pressure. In both DNS-salt and DAS-salt alkali means sodium or potassium.

3 Claims, No Drawings

PROCESS FOR THE PREPARATION OF 4,4'-DIAMINOSTILBENE-2,2'-DISULFONIC ACID OR ITS SALTS

This is a continuation of application Ser. No. 711,725, filed Aug. 11, 1976 now abandoned.

BACKGROUND OF THE INVENTION

Within the last few years, the following patent applications concerning the preparation of DAS and DAS-salt have been laid open or published. These patent applications show that up to the present DAS and DAS-salt have been prepared by catalytic hydrogenation, 1. in the presence of noble metal catalyst (Japanese Patent Publication No. 815/1973)
2. in the presence of both Pd-catalyst and iodine, bromine or their ions (Japanese Provisional Publication (Kokai) No. 127955/1974)
3. in the presence of a metal in Group 8 as a catalyst (German Provisional Publication (Offenlegungsschrift) No. 2320416) (Japanese Kokai No. 12059/1975)
4. in the presence of $MeS_x$ as a catalyst, where $x$ is an integer in the range 1 – 4, inclusive and Me is a metal in Group 8 or Re (Japanese Kokai No. 93927/1975)
5. on cobalt catalyst (German Offenlegungsschrift No. 2362781) (Japanese Kokai No. 93953/1975)
6. in alcohol solvent, in the presence of nickel catalyst (German Offenlegungsschrift No. 2455394) (Japanese Kokai No. 84550/1975)
7. in the presence of nickel catalyst and in aqueous solution of phosphoric acid, boric acid, organic acids or their salts as buffer materials at pH 5 – 10 (Japanese Kokai No. 84551/1975).

In these patent applications, in (1), (2), (3) and (4) noble metal catalysts are employed for the hydrogenation. The noble metal catalysts are much more expensive as compared with Raney nickel catalyst. It is very difficult to recover the noble metal catalysts in good yield in industrial hydrogenation. This raises problems of unprofitability from an economic standpoint. In comparison, Raney nickel catalyst is inexpensive and advantageous for industrial hydrogenation.

In (3) Group 8 metals are employed as catalysts for the hydrogenation of DNS-salt. In example 19 of (3) Raney nickel catalyst is used for comparison. There an unsatisfactory result is obtained, because much 4,4'-diaminodibenzyl-2,2'-disulfonic acid (hereinafter abbreviated as DABS) is formed as a by-product.

In (4) in general higher pressure is needed for the hydrogenation. This is less advantageous for an industrial process. In Control 4c of (4) Raney nickel is used, but the result is unsatisfactory.

In (5) Raney cobalt catalyst is used. It is more expensive than Raney nickel. Higher temperature and higher pressure are necessary for hydrogenation. Therefore this process is less advantageous.

In (6) alcohol which contains less than 3% of water is used as a solvent. The use of such low-water-content alcohol causes elevation of manufacturing cost as compared with the use of water alone as a solvent.

In (7) Raney nickel is used. But higher temperature is needed. The use of inorganic or organic buffer materials often necessitates complicated treatments clarifying discarded water. Such treatments cause elevation of cost for the hydrogenation. Thus in the prior art the use of Raney nickel catalyst in hydrogenation of DNS or DNS-salt gives unsatisfactory results, because DNS or DNS-salt is hydrogenated at the olefinic bond to some degree simultaneously with the nitro groups. This undesirable side reaction occurs considerably when Raney nickel catalyst is used in these prior-art processes.

SUMMARY OF THE INVENTION

In accordance with the present invention, DAS or DAS-salt is obtained in an excellent quality by catalytic hydrogenation of DNS or DNS-salt using Raney nickel catalyst in water in the presence of dicyandiamide.

In this invention the hydrogenation is carried out smoothly and DABS-salt is by-produced only in a minor amount (under suitable conditions less than 0.1%). This result has not been foreseen by the prior art.

DNS or DNS-salt and dicyandiamide are available and can be used for the hydrogenation in this invention.

In this invention the hydrogenation proceeds smoothly and rapidly enough for industrial operation.

The amount of dicyandiamide is preferably used in the range of 0.5 – 50% based upon the weight of DNS or DNS-salt. When an insufficient amount of dicyandiamide is used during the hydrogenation, the olefinic bond of the DNS or DNS-salt is hydrogenated simultaneously with the reduction of the nitro-groups.

The yield of DAS or DAS-salt can be almost quantitative and give 97.5 – 99.0% of the theoretical.

DETAILED DESCRIPTION OF PREFERRED EMBODIMENTS

Under the new catalytic hydrogenation in accordance with this invention, desirable results are obtained by the following procedures. A certain amount of Raney nickel catalyst suspended in water is introduced in an autoclave equipped with a stirrer. Air in the autoclave is replaced by nitrogen and then by hydrogen. The hydrogen pressure is elevated. The content is stirred and heated to the reaction temperature. Measured dicyandiamide is introduced in the autoclave. (The introduction of dicyandiamide may be carried out before the replacement by nitrogen.) Aqueous solution of DNS-salt is fed into the autoclave through a pump and the catalytic hydrogenation is carried out. The hydrogenation is carried out at a temperature in the range of 50° – 120° C, preferably 55° – 90° C. If the reaction is operated at a higher temperature, the hydrogenation results in deterioration of the product, because DABS or DABS-salt and other by-products increase. If the hydrogenation is operated at a temperature below 50° C it takes too long a time to complete the hydrogenation. In this invention the hydrogenation is carried out at an elevated hydrogen pressure. Although it can be carried out at a very high pressure, for example over 100 $kg/cm^2$ (absolute), such a high pressure is unnecessary. It is usually carried out at a pressure in the range between atmospheric pressure and 50 $kg/cm^2$ (absolute), preferably in the range of 5 – 31 $kg/cm^2$ (absolute). It is desirable to control the feeding velocity of DNS or DNS-salt so that substantially no DNS or DNS-salt may be detected in the autoclave during the hydrogenation. If DNS or DNS-salt is fed faster than the hydrogenation velocity, it will remain and increase in the autoclave, and then the hydrogenation does not proceed smoothly and finally stops. After feeding of DNS or DNS-salt is completed the absorption of hydrogen ceases in a few minutes. Then the reaction mixture is cooled. The catalyst is separated by known methods.

The reaction product can be used without any other aftertreatment as an intermediate for optical whitening agents and dyestuffs.

The hydrogenation in this invention is carried out by batch process as explained above and can also be carried out by continuous process.

Further illustration concerning the subject of this invention is shown by the following examples, in which DNS-salt, DAS-salt or DABS-salt means the corresponding sodium salt.

EXAMPLE 1.

0.6 g of Raney nickel catalyst slurried with water (made from 1.5 g of alloy powder), 1.0 g of dicyandiamide and 100 ml of water were fed in a 500 ml capacity autoclave equipped with a stirrer. The lid was closed, air was replaced with nitrogen and then with hydrogen. The hydrogen pressure was elevated to 6 kg/cm$^2$ (absolute) the stirring was started and the temperature was raised to 60° C. Then 140 g of 15.0% aqueous solution of DNS-salt was fed continuously into the autoclave through a pump for 132 minutes. The temperature was maintained at 58° – 62° C and hydrogen was fed to maintain the pressure at 6 kg/cm$^2$ (absolute) during the hydrogenation. After feeding of DNS-salt was completed absorption of hydrogen ceased within a few minutes. The reaction mixture was kept stirring at the same temperature for 10 minutes and then cooled. Stirring was stopped. The hydrogen was replaced with nitrogen. The reaction mixture was separated from the catalyst and analyzed by liquid chromatography. The content of DABS-salt was detected only in trace amounts, which means less than 0.1%, and the main remainder was DAS-salt. The yield of DAS-salt was 97.8% of the theoretical.

EXAMPLE 2.

0.6 g of Raney nickel catalyst slurried with water (made from 1.5 g of alloy powder), 1.0 g of dicyandiamide and 100 ml of water were fed in the 500 ml capacity autoclave used in Example 1. The lid was closed and air was replaced with hydrogen as mentioned in Example 1. The pressure was elevated to 6 kg/cm$^2$ (absolute), the stirring was started and the temperature was raised to 78° C. 98 g of 15.0% aqueous solution of DNS-salt was fed continuously into the autoclave through a pump for 87 minutes at a temperature between 78° – 82° C. Hydrogen was fed to maintain the pressure at 6 kg/cm$^2$ (absolute). The absorption of hydrogen ceased within a few minutes after completion of feeding of DNS-salt. The reaction mixture was kept stirring at the same temperature for 5 minutes, then cooled to 45° C and stirring was stopped. The hydrogen was discharged to the atmospheric pressure and replaced with nitrogen. The reaction mixture was separated from the catalyst and analyzed by liquid chromatography. The content of DABS-salt was 0.4% and the main remainder was DAS-salt. The yield of DAS-salt was 97.5% of the theoretical.

Example 3.

0.6 g of Raney nickel catalyst slurried with water (made from 1.5 g of alloy powder), 2.0 g of dicyandiamide and 100 ml of water were fed in the autoclave used in Example 1. In the same manner as in Example 2, the hydrogen pressure was elevated to 6 kg/cm$^2$ (absolute), the stirring was started and the temperature was raised to 80° C. 100 g of 15.0% aqueous solution of DNS-salt was fed continuously into the autoclave through the pump for 83 minutes at a temperature between 78° – 82° C. Hydrogen was fed to maintain the pressure at 6 kg/cm$^2$ (absolute) during the hydrogenation. The reaction mixture was kept stirring for five minutes after feeding of DNS-salt was completed. Then the autoclave was cooled down. By analysis of the reaction mixture, the content of DABS-salt was 0.4% and the main remainder was DAS-salt. The yield of DAS-salt was 97.5% of the theoretical.

EXAMPLE 4.

0.6 g of Raney nickel catalyst slurried with water (made from 1.5 g of alloy powder), 1.0 g of dicyandiamide and 100 ml of water were fed in the autoclave used in Example 1. In the same manner as in Example 2, the hydrogen pressure was elevated to 11 kg/cm$^2$ (absolute), the stirring was started and the temperature was raised to 80° C. 100 g of 15.0% aqueous solution of DNS-salt was fed continuously into the autoclave for 74 minutes at a temperature between 78° – 82° C. Hydrogen was fed to maintain the pressure at 11 kg/cm$^2$ (absolute) during the hydrogenation. The mixture was kept stirring for 5 minutes after feeding of DNS-salt was completed. Then the reaction mixture was cooled down. By analysis of the reaction mixture the content of DABS-salt was 0.4% and the main remainder was DAS-salt. The yield of DAS-salt was 97.5% of the theoretical.

EXAMPLE 5.

1.0 g of Raney nickel catalyst slurried with water (made from 2.5 g of alloy powder), 100 ml of water were fed in the autoclave used in Example 1. The lid was closed, air was replaced with nitrogen and then with hydrogen. The hydrogen pressure was elevated to 6 kg/cm$^2$ (absolute), the stirring was started and the temperature was raised to 60° C. 0.16 g of dicyandiamide dissolved in 133 ml of 15.0% aqueous solution of DNS-salt (containing 20.0 g of DNS-salt) was fed continuously into the autoclave through the pump for 146 minutes. The temperature was maintained at 58° – 62° C and hydrogen was fed to maintain the pressure at 6 kg/cm$^2$ (absolute) during the hydrogenation. After feeding of DNS-salt was completed, absorption of hydrogen was ceased within a few minutes. The reaction mixture was kept stirring at the same temperature for 10 minutes and then cooled to 40° C. Stirring was stopped. The hydrogen was discharged to atmosphere and replaced by nitrogen. The reaction mixture was separated from the catalyst and analyzed by liquid chromatography. The content of DABS-salt was 0.3% and the remainder was DAS-salt.

EXAMPLES 6 – 9.

The amounts of Raney nickel catalyst showed on Table 1 100 ml of water and the amounts of dicyandiamide showed on Table 1 were fed in the autoclave used in Example 1. The lid was closed and air was replaced with hydrogen as mentioned in Example 1. The pressure was elevated to 6 kg/cm$^2$ (absolute) the stirring was started and the temperature was raised to the reaction temperature, which were showed on Table 1. 133 ml of 15.0% aqueous solution of DNS-salt was fed continuously into the autoclave through the pump and hydrogenated. The temperature was maintained at the temperatures showed on Table 1 and hydrogen was fed to maintain the pressure at 6 kg/cm$^2$ (absolute) during the hydrogenation. After feeding of DNS-salt was completed, absorption of hydrogen was ceased within a few minutes. The reaction mixture was kept stirring at the same temperature for minutes and cooled to 40° C. Stirring was stopped. The hydrogen was discharged to the atmosphere and replaced by nitrogen. The reaction mixture was separated from the catalyst and analyzed by liquid chromatography. The content of DABS-salt was shown on the following Table. Yield of DAS-salt was almost quantitative.

Table 1.

| Example | Cayalyst | Dicyan diamide | DNS-salt |
|---|---|---|---|
| 6 | 15.0 g | 4.0 g | 20.0 g |
| 7 | 10.0 | 10.0 | 20.0 |
| 8 | 3.0 | 1.0 | 20.3 |
| 9 | 6.0 | 2.0 | 20.2 |

| Example | Reaction temperature | DNS-salt feeding time | DAS-salt yield % | Content of DABS-salt % |
|---|---|---|---|---|
| | | minutes | | |
| 6 | 59–61° C | 29 | 98.7 | 0.3 |
| 7 | 69–71 | 91 | 98.5 | 0.6 |
| 8 | 59–61 | 90 | 98.8 | 0.4 |
| 9 | 59–61 | 41 | 98.8 | 0.4 |

CONTROL 1.

0.6 g of Raney nickel catalyst slurried with water (made from 1.5 g of alloy powder) and 100 ml of water were fed in the 500 ml capacity autoclave used in Example 1. In the same manner as in Example 1, the hydrogen pressure was elevated to 11 kg/cm$^2$ (absolute), the stirring was started and the temperature was raised to 80° C. 92 g of 15.0% aqueous solution of DNS-salt was fed continuously into the autoclave through the pump for 90 minutes. The hydrogenation was carried out at a pressure of 11 kg/cm$^2$ (absolute). After feeding of DNS-salt was completed, the reaction mixture was kept stirring for five minutes at 80° C and then cooled down. The reaction mixture was analyzed by liquid chromatography. The content of DABS-salt was 13.7% and DAS-salt was 86.3%.

CONTROL 2.

0.6 g of Raney nickel catalyst slurried with water (made from 1.5 g of alloy powder) and 100 ml of water were fed in the 500 ml capacity autoclave used in Example 1. In the same manner as in Example 1, the hydrogen pressure was elevated to 6 kg/cm$^2$ (absolute), the stirring was started and the temperature was raised to 80° C. 113 g of 15.0% aqueous solution of DNS-salt was fed continuously into the autoclave through the pump for 90 minutes. The hydrogenation was carried out at a temperature between 78° – 82° C. Absorption of hydrogen ceased within a few minutes after feeding of DNS-salt was completed. The reaction mixture was kept stirring for five minutes at the reaction temperature and cooled. By analysis of the reaction mixture, DABS-salt was 6.7% and DAS-salt was 93.3%.

We claim:

1. A process for the preparation of 4,4'-diaminostilbene-2,2'-disulfonic acid or its alkali salts which comprises catalytic hydrogenation of 4,4'-dinitrostilbene-2,2'-disulfonic acid or its alkali salts in the presence of both Raney nickel and dicyandiamide in water at a temperature in the range of 50° to 120° C under an elevated hydrogen pressure, the amount of dicyandiamide being from 0.5 to 50% by weight of 4,4'-dinitrostilbene-2,2'-disulfonic acid or its alkali salts.

2. A process as claimed in claim 1 wherein the hydrogen pressure is from atmospheric pressure to 50 kg/cm$^2$ (absolute).

3. A process as claimed in claim 1 wherein said alkali salt of 4,4'-dinitrostilbene-2,2'-disulfonic acid is sodium salt.

* * * * *